United States Patent
Davis et al.

(10) Patent No.: US 10,261,048 B2
(45) Date of Patent: Apr. 16, 2019

(54) SPATIALLY ALTERNATING ASYMMETRIC FIELD ION MOBILITY SPECTROMETER

(71) Applicant: SensIT Ventures, Inc., Davis, CA (US)

(72) Inventors: Cristina E. Davis, Davis, CA (US); Alexander A. Aksenov, Davis, CA (US); Yuriy Zrodnikov, Davis, CA (US)

(73) Assignee: SENSIT VENTURES, INC., Davis, CA (US)

( * ) Notice: Subject to any disclaimer, the term of this patent is extended or adjusted under 35 U.S.C. 154(b) by 0 days.

(21) Appl. No.: 14/410,960

(22) PCT Filed: Aug. 30, 2013

(86) PCT No.: PCT/US2013/057626
§ 371 (c)(1),
(2) Date: Dec. 23, 2014

(87) PCT Pub. No.: WO2014/036465
PCT Pub. Date: Mar. 6, 2014

(65) Prior Publication Data
US 2015/0323500 A1    Nov. 12, 2015

Related U.S. Application Data

(60) Provisional application No. 61/695,642, filed on Aug. 31, 2012.

(51) Int. Cl.
*G01N 27/62* (2006.01)
*H01J 49/00* (2006.01)
*H01J 49/06* (2006.01)
*H01J 49/42* (2006.01)

(52) U.S. Cl.
CPC ......... *G01N 27/624* (2013.01); *G01N 27/622* (2013.01); *H01J 49/062* (2013.01); *H01J 49/065* (2013.01); *H01J 49/4235* (2013.01); *Y10T 29/49119* (2015.01)

(58) Field of Classification Search
None
See application file for complete search history.

(56) References Cited

U.S. PATENT DOCUMENTS

| | | |
|---|---|---|
| 6,193,866 B1 | 2/2001 | Bader et al. |
| 6,888,130 B1 | 3/2005 | Gonin |
| 7,084,394 B2 * | 8/2006 | Guevremont ............. H01J 9/42 250/282 |

(Continued)

*Primary Examiner* — Michael J Logie (57) ABSTRACT

One embodiment of the present disclosure provides an ion mobility spectrometry (IMS) device for performing chemical analysis. The IMS device includes a first set of electrodes arranged linearly in a first direction and separated by a first set of gaps. The IMS device includes a second set of electrodes positioned directly opposing the first set of electrodes to match the first set of electrodes on a one-to-one basis, wherein the second set of electrodes are separated by a second set of gaps. The IMS device includes a drift region between the first set of electrodes and the second set of electrodes, wherein charged particles enter at a first end of the drift region and traverse the drift region along the first direction. The IMS device additionally includes a detector positioned at a second end of the drift region and configured to receive charged particles exiting the drift region.

18 Claims, 8 Drawing Sheets

(56) References Cited

U.S. PATENT DOCUMENTS

| | | | |
|---|---|---|---|
| 7,351,961 B2* | 4/2008 | Malek | H01J 49/38 250/281 |
| 2003/0146377 A1 | 8/2003 | Miller et al. | |
| 2004/0144918 A1 | 7/2004 | Zare et al. | |
| 2006/0097156 A1* | 5/2006 | Guevremont | G01N 27/624 250/290 |
| 2006/0192102 A1* | 8/2006 | Miller | G01N 27/624 250/286 |
| 2008/0210861 A1* | 9/2008 | Wu | G01N 27/624 250/287 |
| 2009/0173880 A1* | 7/2009 | Bateman | H01J 49/065 250/292 |
| 2009/0189064 A1* | 7/2009 | Miller | G01N 27/624 250/282 |
| 2009/0294655 A1* | 12/2009 | Ding | H01J 49/004 250/283 |
| 2009/0321655 A1* | 12/2009 | Makarov | H01J 49/065 250/396 R |
| 2010/0314548 A1* | 12/2010 | Munchmeyer | G01N 27/624 250/375 |
| 2011/0001044 A1* | 1/2011 | Chou | G01N 27/622 250/282 |
| 2011/0095175 A1* | 4/2011 | Bateman | G01N 27/624 250/282 |
| 2011/0180702 A1* | 7/2011 | Flory | H01J 49/406 250/282 |
| 2012/0018631 A1* | 1/2012 | Giles | G01N 27/624 250/282 |
| 2014/0127672 A1* | 5/2014 | Davis | C12Q 1/6895 435/5 |
| 2014/0299761 A1* | 10/2014 | Giles | H01J 49/421 250/283 |
| 2015/0028196 A1* | 1/2015 | Toutoungi | G01N 27/624 250/281 |

\* cited by examiner

SPATIALLY ALTERNATING ASYMMETRIC FIELD ION MOBILITY SPECTROMETER

BACKGROUND

Field

The present disclosure generally relates to the design of Ion Mobility Spectrometer (IMS). More specifically, the present disclosure relates to design of a Spatially Alternating Asymmetric Field Ion Mobility Spectrometry (SAAF IMS) which allows for direct current (DC)-only control of the device operation, and various hybrid high-Field Asymmetric Ion Mobility Spectrometer (FAIMS)/IMS devices which allow for direct DC-only control of both FAIMS and IMS ion detection.

Related Art

Ion Mobility Spectrometer (IMS) is an analytical device for separating and identifying ionized molecules in the gas phase based on their mobility in a carrier buffer gas. In a traditional IMS device, ionized species in a carrier gas travel through a drift tube which applies an electric field to the ions. The separation of gas-phase ions occurs within the drift tube based on the different ion mobility of the ionized species. Typically, ion mobility is a function of both the applied electric field and gas density. By measuring time for ions to travel from one side of the drift tube to another, velocity can be determined. A special type of IMS is a high-Field Asymmetric Ion Mobility Spectrometer (FAIMS), which is capable of separating gas-phase ions at atmospheric pressure and at room temperature. Typically, FAIMS uses time-varying, high-voltage, high-frequency electric field to separate ions based on the fact that ion mobility depends on the non-linearity of the field.

However, because FAIMS requires using a waveform generator to generate the high-strength, high-frequency field, FAIMS typically has high power consumption. In addition, FAIMS requires a gas propulsion system to drive the carrier gas. Unfortunately, use of a gas propulsion system and waveform generator hinders the ability to reduce the physical dimension of FAIMS into portable devices.

Hence, what is needed is IMS device that is capable of performing FAIMS functions without the problems described above.

SUMMARY

One embodiment of the present disclosure provides an ion mobility spectrometry (IMS) device for performing chemical analysis. The IMS device includes a first set of electrodes arranged linearly in a first direction and separated by a first set of gaps. The IMS device also includes a second set of electrodes positioned directly opposing the first set of electrodes to match the first set of electrodes on a one-to-one basis, wherein the second set of electrodes are separated by a second set of gaps. The IMS device includes a drift region between the first set of electrodes and the second set of electrodes, wherein charged particles enter at a first end of the drift region and traverse the drift region along the first direction. The IMS device additionally includes a detector positioned at a second end of the drift region and configured to receive charged particles exiting the drift region.

In some embodiments, a first electrode in the first set of electrodes and a matching first electrode in the second set of electrodes generate a first electric field perpendicular to the first direction. A second electrode in the first set of electrodes and a matching second electrode in the second set of electrodes create a second electric field having an opposite polarity to the first electric field. The first set of electrodes and the second set of electrodes create a field pattern which spatially alternates between the first electric field and second electric field along the first direction. The charged particles traverse the drift region along the first direction.

In some embodiments, the first set of electrodes includes electrodes which have at least two different lengths.

In some embodiments, both the first electric field and the second electric field are static electric fields.

In some embodiments, the first set of electrodes includes electrodes which alternate between a first length and a second length that is less than the first length. The first electrode in the first set of electrodes is of the first length and the second electrode in the first set of electrodes is of the second length. The second set of electrodes includes matching electrodes which alternate between the first length and the second length. The matching first electrode in the second set of electrodes is of the first length and the matching second electrode in the second set of electrodes is of the second length.

In some embodiments, the second electrode is coupled to a positive DC voltage $V_1$ and the matching second electrode is coupled to a negative DC voltage $-V_1$. Meanwhile, the first electrode is coupled to a negative DC voltage $-V_2$ and the matching first electrode is coupled to a positive DC voltage $V_2$. Note that $V_1$ is greater than $V_2$.

In some embodiments, $E_1L_1+E_2L_2$ is substantially equal to zero, wherein $E_1$ and $E_2$ are the first and second electric fields, respectively, and $L_1$ and $L_2$ are the lengths of the first electrode and the second electrode, respectively.

In some embodiments, the first set of electrodes is disposed on a first electrode plane; the second set of electrodes is disposed on a second electrode plane; and the distance between the first electrode plane and the second electrode plane determines a gap between each pair of opposing electrodes.

In some embodiments, the spatially alternating first electric field and second electric field are configured to cause charged particles of different mobility dependences on the first and second electric fields to separate by deflecting toward one of the first and second sets of electrodes while traversing the drift region.

In some embodiments, the spatially alternating first electric field and second electric field are configured so that charged particles of different mobility dependences are most fully separated while traversing the full length of the drift region.

In some embodiments, a compensating voltage (CV) is applied to all of the electrodes in the first set of electrodes or the second set of electrodes to correct a path of a charged particle to allow the charged particle to exit the drift region in such a way as to properly hit the detector.

In some embodiments, a subset of electrodes in the first set of electrodes and the matching electrodes in the second set of electrodes are coupled to a set of offset voltages to create an electric field gradient through the drift region for propelling the charged particles.

In some embodiments, a gating pulse generating mechanism is configured to generate a timed gating pulse on one or more pairs of opposing electrodes for driving charged particles longitudinally.

In some embodiments, the timed gating pulses are timed to relay ions with mobility within a target range longitudinally while stopping charged particles having mobility outside of the target range.

In some embodiments, the voltage of the timed gating pulses is selected so as to enable the fastest possible longitudinal ion drift while avoiding ion heating and concomitant chemical transformation.

In some embodiments, the voltage of the timed gating pulses is selected so as to enable the fastest possible longitudinal ion drift while avoiding ion heating and concomitant chemical transformation.

In some embodiments, the resolution of a differential mobility separation of the IMS device is increased due to reduced ion residence time as a result of minimized time of ions traversing the drift region.

In some embodiments, the first set of gaps is a first constant gap and the second set of gaps is a second constant gap, and the first constant gap is substantially equal to the second constant gap.

In some embodiments, the device does not require a waveform generator.

In some embodiments, the IMS device is configured to output the following signals associated with a given type of ion: a drift time; a compensation voltage associated with a differential mobility-based parameter; and an ion abundance parameter.

In some embodiments, the IMS device further includes a controller configured to scan the first electric field while keeping the ratio of the first electric field and the second electric field constant. The IMS device is configured to output the scanning signal generated by the controller.

In some embodiments, the IMS device also includes ion reflectrons positioned at both ends of the drift region, wherein the ion reflectrons are configured to reflect the arriving charged particles back through the drift region to enhance the resolution of differential mobility separation.

In some embodiments, the first set of electrodes and the second set of electrodes are fabricated through a microfabrication process. The first set of electrodes and the second set of electrodes can be fabricated from the same wafer, which involves fabricating a first set of electrical wires interconnecting the first set of electrodes and a second set of electrical wires interconnecting the second set of electrodes on the same wafer.

In some embodiments, the IMS device also includes a driving mechanism positioned at the first end of the drift region and configured to drive the charged particles into the drift region.

BRIEF DESCRIPTION OF THE FIGURES

Note that like reference numerals refer to corresponding parts throughout the drawings. Moreover, multiple instances of the same part are designated by a common prefix separated from an instance number by a dash.

DETAILED DESCRIPTION

Embodiments of the present disclosure provide an Ion Mobility Spectrometer (IMS) design based on using micro-scale discrete electrodes that are spatially distributed in two parallel planes. Rather than using a time-varying, high-strength, high-frequency electric field as in a FAIMS device, spatially varying direct current (DC) voltages are applied to two planes of opposing discrete electrodes to create alternating low-field and high-field regions and alternating field polarity regions in the drift region. The created spatially varying electric fields and spatial non-linearity of the electric fields in the drift region facilitate separating ions via a non-linear mobility process. In one embodiment, the discrete electrodes are configured as alternating "short" and "long" electrodes.

Furthermore, rather than using carrier gas to propel ions through the drift region, different ion propulsion techniques that do not involve carrier gas are proposed. In one embodiment, ions are propelled through the drift region electrostatically by a field gradient which is created by DC offset voltages applied to the discrete electrodes. In another embodiment, timed DC voltages are applied to the discrete electrodes to generate timed low field pulses which enable timed ion propulsion through the drift region. We now describe embodiments of the proposed IMS devices. In the discussion below, terms "drift tube" and "drift region" are used interchangeably. Also, terms "charged particles" and "ions" are used interchangeably.

Figure 1:
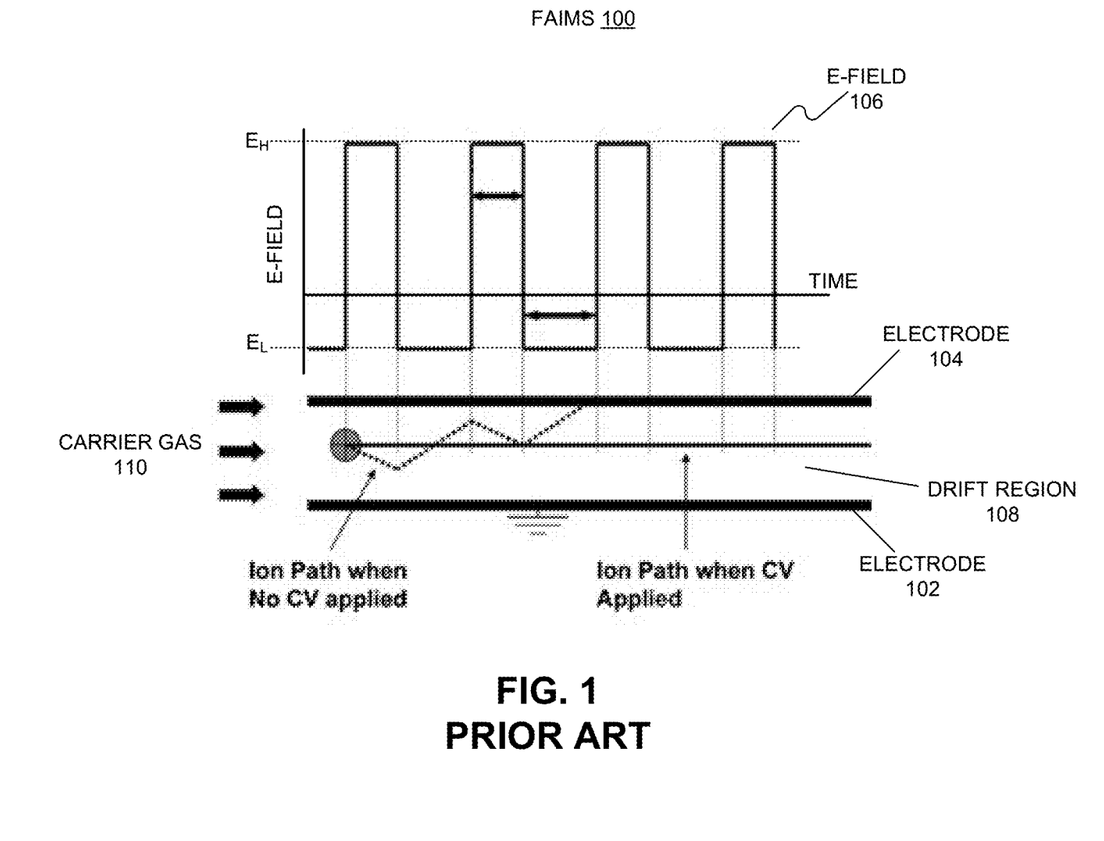
FIG. 1 illustrates a conventional FAIMS for chemical sensing.

FIG. 1 illustrates a conventional FAIMS 100 for chemical sensing. As can be seen, FAIMS 100 comprises two electrodes: electrode 102 which is grounded, and electrode 104 which is connected to a waveform generator that generates time-varying electric field 106. Both electrodes 102 and 104 can be planar electrodes, and space between the two electrodes defines a drift region 108. A carrier gas 110 carrying ion species enters drift region 108 from the left. Note that E-field 106 alternates between a high strength E-field $E_H$ and a low strength E-field $E_L$. For a given ion species, its mobility is insensitive to the low strength field $E_L$, but is non-linearly dependent on the high strength E-field $E_H$. For example, the low strength E-field mobility and the high strength E-field mobility may be expressed by Eqn. (1) and Eqn. (2) below:

$$K(E) = K(0) \tag{1}$$

$$K(E) = K(0)\left[1 + a\left(\frac{E}{N}\right)^2 + b\left(\frac{E}{N}\right)^4 + c\left(\frac{E}{N}\right)^6 + \ldots\right] \tag{2}$$

Figure 2A:
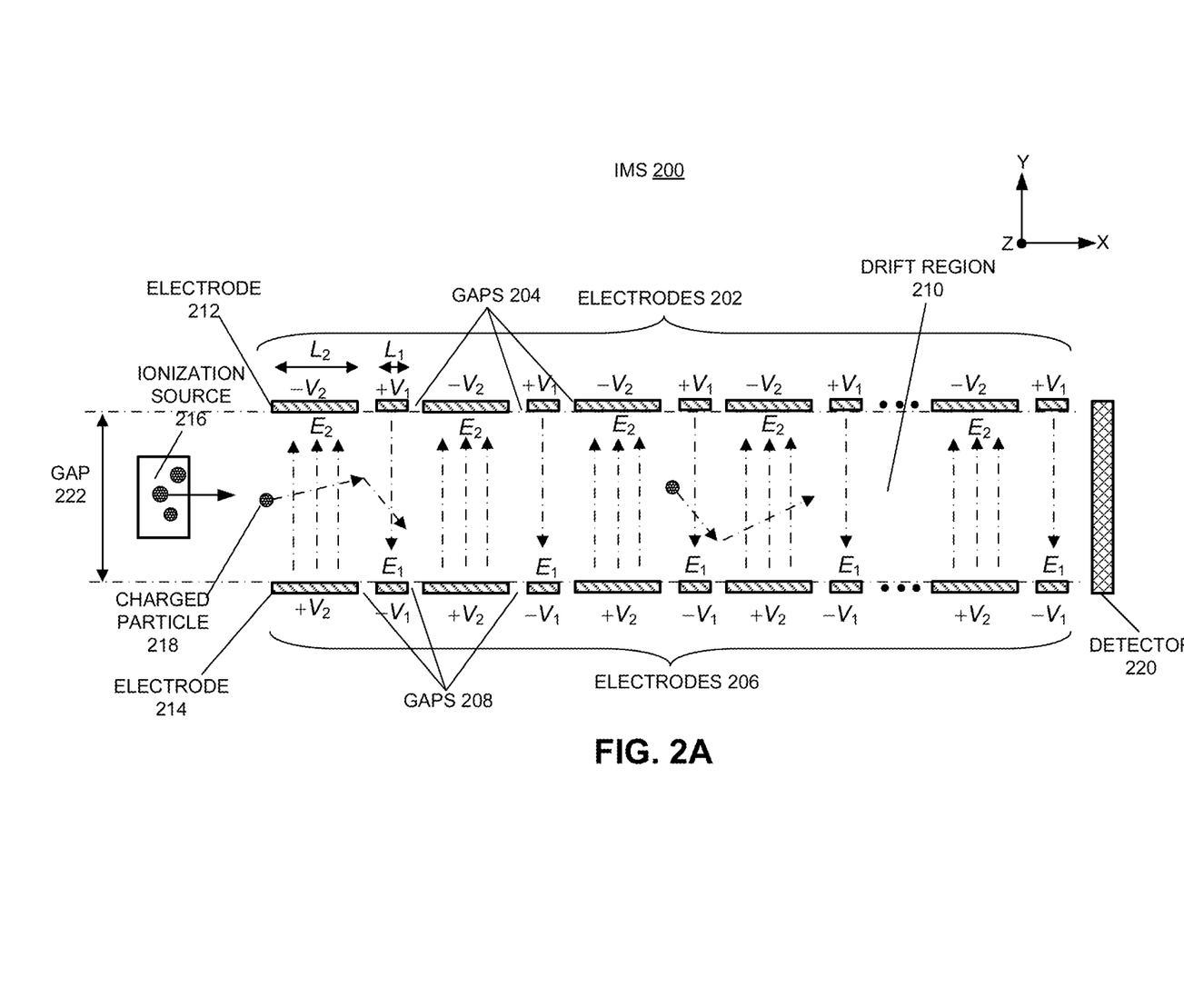
FIG. 2A presents a cross-sectional view of a Spatially Alternating Asymmetric Field Ion Mobility Spectrometry (SAAF IMS) in accordance with an embodiment of the present disclosure.

FIG. 2A presents a cross-sectional view of a Spatially Alternating Asymmetric Field Ion Mobility Spectrometry (SAAF IMS) 200 in accordance with an embodiment of the present disclosure. As can be seen in FIG. 2A, SAAF IMS 200 (or "IMS 200") includes two parallel planes oriented horizontally in the x-direction, each of which is formed by a linear array of discrete electrodes. A drift region 210 is formed between the two parallel planes. More specifically, the first set of alternating short and long electrodes 202 is arranged in a linear series and separated by a first set of gaps 204 between each adjacent short and long electrode. In one embodiment, these gaps are of a micro-scale that is less than 1 mm. The first set of discrete electrodes 202 forms the first plane of drift region 210. The second set of short and long electrodes 206 is arranged in parallel and directly opposing the first set of electrodes 202 so that opposing short-short and long-long electrodes in the first and second sets of electrodes face each other on a one-to-one basis. Note that the second set of electrodes 206 is separated by a second set of gaps 208 which matches the first set of gaps 204. The second set of electrodes 206 forms the second plane of drift region 210, which has a constant size gap between the two planes. In the embodiment shown, an electrode (such as long electrode 212) in the first set of electrodes 202 and a matching electrode (e.g., long electrode 214) in the second set of electrodes 206 have the same dimensions both in the visible x-dimension and the invisible z-dimension. Note that a voltage is applied to each electrode in both the first and second sets of electrodes 202 and 206 to create regions of alternating electric fields within drift region 210.

In the embodiment shown, each set of electrodes comprises alternating short electrodes of length $L_1$ and long electrodes of length $L_2$. Hence, a long electrode is adjacent to two short electrodes and a short electrode is adjacent to two long electrodes. In other embodiments, each set of electrodes can use the similar short and long electrodes but arranged in configurations other than repeating "short-long-short-long." For example, a set of electrodes can be arranged in repeating "short-long-long-short-long-long" or in repeating "long-short-short-long-short-short" configurations. Note that while each set of electrodes 202 and 206 comprises only two electrode lengths in the x-direction, other embodiments may have each set of electrodes configured with more than two lengths, for example, in three different lengths $L_1$, $L_2$ and $L_3$ in the x-direction.

Figure 2B:
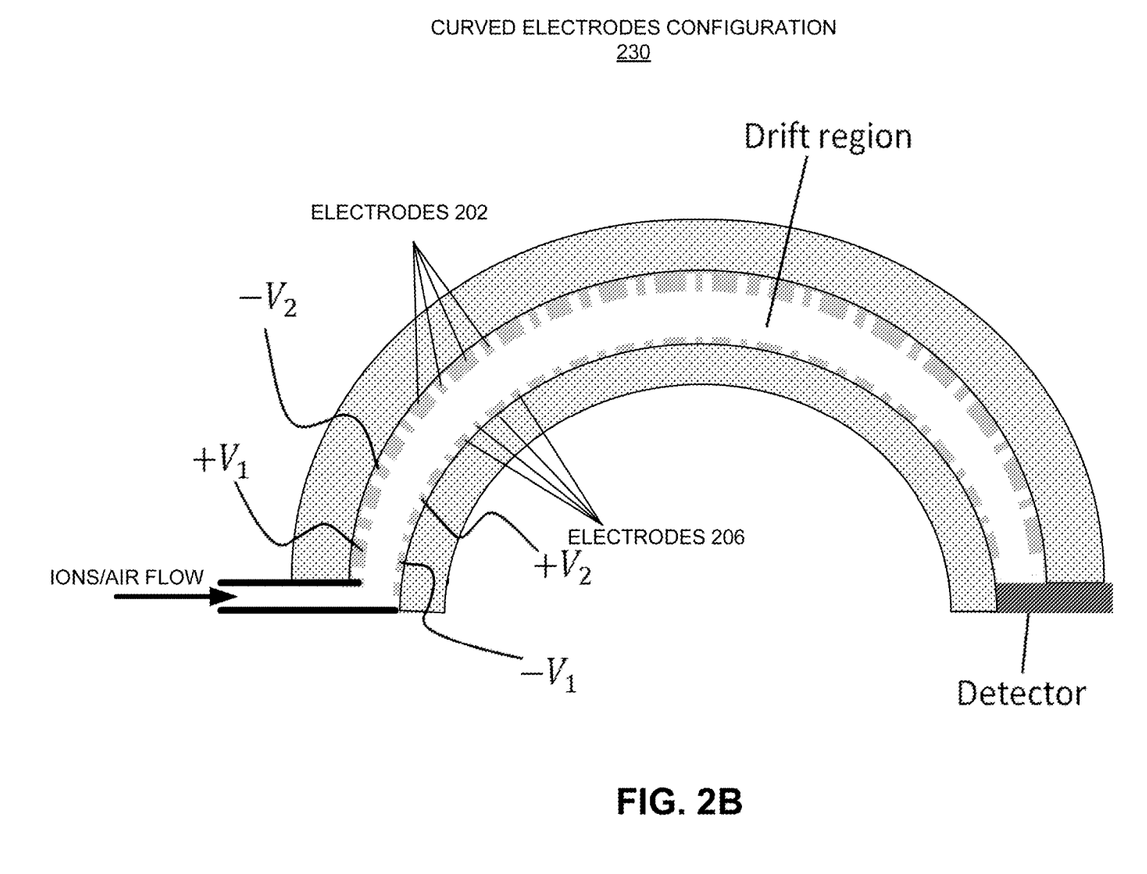
FIG. 2B illustrates an exemplary curved electrodes configuration in accordance with an embodiment of the present disclosure.

Note that each electrode in the sets of electrodes 202 and 206 can be a planar electrode such that it has a straight line profile in the invisible z-direction. However, in some embodiments, the sets of electrodes 202 and 206 can be formed by curved electrodes. For example, each of these electrodes can have a curved profile in the y-z plane. In one embodiment, a matching electrode pair in the sets of electrodes 202 and 206 can have concentric curvatures in the y-z plane. FIG. 2B illustrates an exemplary curved electrodes configuration 230 in accordance with an embodiment of the present disclosure. Curved electrodes configuration 230 is based on FAIMS devices which use concentric cylindrical electrodes. However, instead of using monolithic upper and lower electrodes, curved electrodes configuration 230 uses two discrete sets of electrodes 202 and 206 of two alternating lengths to implement the concentric cylindrical electrode configuration. Such configuration has the benefit of ion focusing at the outlet due to non-linear field in such arrangement and is particularly useful for FAIMS devices used as a prefilter for mass spectrometry. In general, as long as the two sets of electrodes 202 and 206 are electrically isolated from each other, various electrode shapes can be used. Hence, the present disclosure is limited to using planar electrodes as the discrete electrodes.

Further, while the embodiment of FIG. 2A illustrates a specific number of discrete electrodes in each set of electrodes, other embodiments of the sets of electrodes can have any number of discrete electrodes but is typically a number greater than 10. One skilled in the art will appreciate that there can be numerous geometrical variations to the sets of electrodes 202 and 206. While the following discussion is based on using the alternating short and long electrodes, the general concepts of this disclosure are equally applicable to discrete electrodes of other configurations than the one shown in FIG. 2A.

Referring back to FIG. 2A, note that a pair of opposing short electrodes is electrically coupled to DC voltages (also referred to as "potentials" hereinafter) $+V_1$ and $-V_1$ to create a first static electric field $E_1$ between the pair of short electrodes. More specifically, the upper short electrode is coupled to a positive DC voltage $+V_1$ to become positively charged and a lower short electrode is coupled to a negative DC voltage $-V_1$ to become negatively charged, and field $E_1$ has a polarity in the negative y direction. Similarly, a pair of long electrodes is coupled to DC voltages $+V_2$ and $-V_2$ to create a second static electric field $E_2$ between the pair of long electrodes. More specifically, the upper long electrode is coupled to a negative DC voltage $-V_2$ to become negatively charged and the lower long electrode is coupled to a positive DC voltage $+V_2$ to become positively charged, and field $E_2$ has a polarity in the positive y direction. Hence, the sets of electrodes and the associated voltage configuration create a static electric field distribution of alternating field polarity.

In one embodiment, potential $V_1$ is greater than $V_2$; therefore, field $E_1$ is stronger than $E_2$. Hence, the sets of electrodes 202 and 206, and the associated voltage configuration between them create a static field distribution of alternating high- and low-strength electric field regions within drift region 210, in addition to the alternating field polarity. Note that such alternating high- and low-strength electric field and alternating field polarity create necessary non-linearity for discriminating different ion species. Moreover, the field non-homogeneity due to the fringe-effects of non-infinite electrodes will create additional non-linearity useful for ion separation.

Note that the electrode potentials should be set to values that will result in field strengths $E_1$ and $E_2$ that will facilitate ion separation. In some embodiments, $E_1$ is significantly greater than $E_2$ to create a greater non-linearity in field distribution inside drift region 210. The potentials on the electrodes may be set to achieve maximum and minimum possible field strengths allowable by the device geometry. In some embodiments, the maximum high-field value $E_1$ is limited by the electric breakdown potential of the actual electrodes, while the low-field value $E_2$ is limited by the device geometry. In one embodiment, the geometry ratio of long and short electrodes $L_2/L_1$ is used to determine the field strength $E_1$ and $E_2$. In a particular embodiment, $E_1 = -E_2 \times (L_2/L_1)$, i.e., $E_1L_1 + E_2L_2$ is substantially equal to zero. In some embodiments, the suggested range of $L_2/L_1$ is in the order of 10 to 30 or higher. For example, if $L_2/L_1 = 20$, then the magnitude of $E_1$ is 20 times that of $E_2$. Note that the potentials on the electrodes may be adjusted to correct for non-uniformity of the field, especially in between short sets of electrodes.

In one embodiment, the two sets of electrodes 202 and 206 are micro-fabricated from the same wafer, and brought together to form IMS 200 and drift region 210. Due to micro-fabrication, gap 222 between the two sets of electrodes 202 and 206 is also in the micro-scale. In some embodiments, gap 222 can have a size from a few microns to a few hundred microns. Due to this micro-scale gap of IMS 200, only a low DC voltage $V_1$ is required to generate a sufficiently high field $E_1$. For example, $V_1$ can be 20V while $V_2$ is 1V. Consequently, IMS 200, which only needs low DC voltages, uses significantly less power than traditional FAIMS devices which require high frequency wave form generator.

Note that ion separation in drift region 210 may occur primarily within high-strength field regions between short sets of electrodes. Equations (1) and (2) indicate that in very low-strength field regions between long sets of electrodes, the ion mobility of a given ion species is not dependent on the field strength. However, in high-strength field regions between short sets of electrodes, the ion mobility of a given ion species has a non-linear dependency on the field strength $E_1$. This non-linear dependency allows different ion species to separate as they traverse drift region 210 and the amount of separation generally increases as field strength $E_1$ increases.

In one embodiment, the spatially alternating electric field distribution within drift region 210 is configured to cause charged particles of different mobility dependences on $E_1$ to separate in both the +y and −y directions.

FIG. 2A also illustrates an ionization source 216 to the left of drift region 210. Ionization source 216 can be a radioactive source, for example 63Ni, as well as a non-radioactive source. As sample particles are passed through ionization source 216, they typically gain an ionic charge and become charged particles. Charged particles (also referred to as "ions of interest" hereinafter), such as charged particle 218, are then introduced into drift region 210. In one embodiment, a specified voltage with polarity matching that of the ions of interest is applied to a pusher plate (not shown), which will deflect the ions of interest and introduce them into the drift tube. The initial drift speed of the ions of interest can be precisely controlled by varying the voltage on the pusher plate.

As can be seen in FIG. 2A. IMS 200 also includes a detector 220 to the right of drift region 210. While FIG. 2A shows that detector 220 is located outside drift region 210, other embodiments can have the detector placed at the very end of the drift region. Detector 220 functions to record the presence of an ion which has traveled through the entire drift region 210. Many types of detectors, for example a current amplifier, may be used as detector 220.

We now describe how charged particles are moved through drift region 210 which is configured with the spatially alternating field polarity and strength shown in FIG. 2A.

Further referring to FIG. 2A, note that after ionization, charged particle 218 is introduced into drift region 210 from the left and will move through drift region 210 toward detector 220 located at the exit of drift region 210. As charged particle 218 traverses the length of drift region 210, charged particle 218 experiences two distinct electrostatic forces in the y-direction which cause alternating displacements toward upper and lower electrodes. The first displacement takes place when charged particle 218 traverses low-strength field $E_2$ regions between the long sets of electrodes. Depending on the polarity of charged particle 218, it may displace either in the positive y-direction or in the negative y-direction. In the example shown, charged particle 218 is positively charged so that it will displace in the positive y-direction in the low-strength $E_2$ regions.

The second displacement takes place when charged particle 218 traverses high-strength field $E_1$ regions between the short sets of electrodes. Depending on the polarity of charged particle 218, it may displace either in the positive y-direction or in the negative y-direction, but in an opposite direction to its displacement in the low-strength $E_2$ regions. In the example shown, positively charged particle 218 will displace in the negative y-direction in the high-strength $E_1$ regions. Hence, charged particle 218 will displace up and down in a "zigzag" motion as it traverses from the left to the right of drift region 210. Note that when alternating displacements cancel each other out, charged particle 218 can traverse the entire drift region without being neutralized on the electrodes. When these displacements do not cancel out for an ion of interest, an additional compensation voltage (CV) may be applied to all of the upper set of electrodes 202 or all of the lower set of electrodes 206 to correct the path for the ion of interest. On the other hand, by keeping CV at a set value, IMS 200 will allow only a subset of ions to pass through drift region 210, eliminating the rest on the electrodes along with way. As in traditional FAIMS, scanning CV will produce a plot of ion abundance versus CV.

We now describe different techniques of propelling ions of interest from left to right through the drift region 210 which is configured with the alternating field polarity and strength shown in FIG. 2A.

Figure 3:
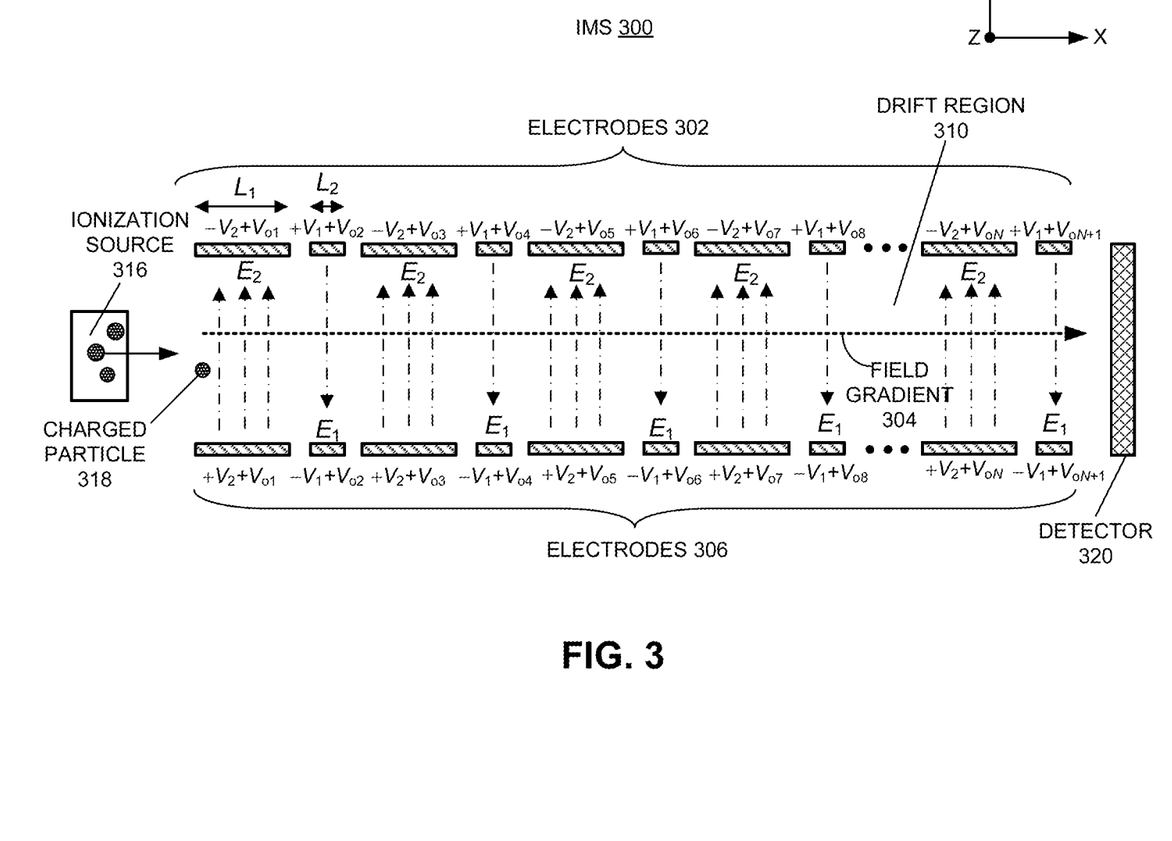
FIG. 3 illustrates an IMS which is configured with an exemplary field configuration which superimposes the static electric field described in FIG. 2A with a field gradient in accordance with an embodiment of the present disclosure.

Note that in traditional FAIMS, ions are carried through the device by a flow of carrier gas. In some embodiments of the present disclosure, charged particles are propelled through the drift region electrostatically by a field gradient which is configured to be oriented in the x-direction, wherein the field gradient is superimposed with the static DC field of $E_1$ and $E_2$. FIG. 3 illustrates an IMS 300 which is configured with an exemplary field configuration which superimposes the static electric field described in FIG. 2A with a field gradient in accordance with an embodiment of the present disclosure. Note that IMS device 300 does not require carrier gas for ion propulsion. As can be seen, IMS 300 comprises the same electrode configuration and same alternating DC field configuration as IMS 200. A charged particle 318 generated by an ionization source 316 is introduced into a drift region 310, and will reach detector 320 is selected by IMS 300. An electric field gradient 304 in drift region 310 is achieved by applying an additional offset voltage to each electrode so that the offset is superimposed onto the DC voltages which are used to displace the ions in the up and down directions.

More specifically, the upper set of electrodes 302 in IMS 300 is offset by a set of positive voltages $+V_{o1}$, $+V_{o2}$, $+V_{o3}$, etc., from left to right, wherein the offset voltages $+V_{o1}$, $+V_{o2}$, $+V_{o3}$, etc., monotonically decrease in value. For example, the first long electrode at the upper left has a combined DC voltage of $-V_2+V_{o1}$, and the first short electrode at the upper left has a combined DC voltage of $+V_1+V_{o2}$, wherein $V_{o2}<V_{o1}$, etc. Similarly, the lower set of electrodes 306 is offset by the same set of positive voltages $+V_{o1}$, $+V_{o2}$, $+V_{o3}$, etc., from left to right, so that each pair of opposing electrodes is offset by the same amount. For example, the first long electrode at the lower left has a combined DC voltage of $+V_2+V_{o1}$, and the first short electrode at the lower left has a combined DC voltage of $-V_1+V_{o2}$, wherein $V_{o2}<V_{o1}$, etc. Hence, the sets of superimposed DC offset voltages create field gradient 304 which points from left to right within drift region 310, which will facilitate sweeping a positive ion from left to right through drift region 310.

Note that the superimposed field gradient 304 is independent of the alternating DC field distribution of the low and high fields $E_1$ and $E_2$. Note also that the IMS device 300 does not require carrier gas for ion propulsion purposes. Because neither an RF waveform generator nor a carrier gas preparation system is needed in IMS device 300, the physical dimensions of IMS 300 are not significantly different from the size of drift region 310. In one embodiment of IMS 300, drift region 310 and IMS device 300 are a few centimeters in length and less than 1 mm in thickness. Moreover, by getting rid of the carrier gas preparation system, IMS device 300 does not need pumps or have other moving parts, thereby leading to greater robustness of the device. Because IMS device 300 can be mass produced by micro-fabrication alone, the cost of device manufacturing is expected to be extremely low. The sensitivity of the device can be increased by simply stacking multiple of these chip-sized units.

Although the embodiment of FIG. 3 describes a field gradient created by applying offset voltages to all discrete electrodes in IMS 300, many other variations to this embodiment can be used to generate the field gradient. In one embodiment, the DC offset voltages are only applied to the short set of electrodes. In another embodiment, the DC offset voltages are only applied to the long set of electrodes. A person skilled in the art will appreciate that there are many other obvious variations on how to superimpose the offset voltages on the sets of discrete electrodes to achieve the required field gradient. In one embodiment, the potential on each electrode in the sets of electrodes 302 and 306 can be controlled separately. This would allow individual adjustment of the drift path of an ion of interest at different locations within drift region 310.

Furthermore, while the embodiment of FIG. 3 describes a field gradient created for positive ions, IMS 300 may be easily configured to perform separate ion propulsions for both positive and negative ions, by changing the direction of the field gradient.

In one embodiment, instead of creating the field gradient by superimposing the offset voltages on sets of electrodes 302 and 306, dedicated electrode pairs may be provided to achieve the same field gradient. For example, while sets of electrodes 302 and 306 define the top and bottom planes of drift region 310, third and fourth sets of discrete electrodes may be positioned perpendicular to the sets of electrodes 302 and 306 to define front and back planes of drift region 310. Then, the decreasing DC voltages are directed applied to pairs of the third and fourth sets of discrete electrodes to create the required field gradient, while the DC voltages on the sets of electrodes 302 and 306 are unchanged.

In some embodiments, charged particles are propelled through the drift region electrostatically by timed "pusher" fields applied to selected pairs of opposing electrodes. In these embodiments, when an ion of interest passes through a pair of opposing electrodes and leaves the associated field region, a potential matching of the polarity of the ion of interest may be applied to both the upper and lower electrodes, thereby causing the ion to be repelled from the electrodes and continue on its directed path forward through the drift region. A timed pusher field is configured as a short pulse; after the short interval of the pulse, the voltages on the pair of electrodes are switched back to normal DC +/− voltages and the field $E_1$ or $E_2$ is restored. Note that such a timed pusher field may be repeated on multiple sets of opposing electrodes. For example, the pusher pulses may be applied to only short sets of electrodes. Hence, as an ion of interest moves through the drift region, the pusher pulse is applied to a given pair of opposing short electrodes as soon as the ion of interest clears that given set of short electrodes. However, no pusher pulse will be applied to a pair of long electrodes after the ion of interest passes through the pair of long electrodes. In other embodiments, the pusher pulses may be applied only to pairs of opposing long electrodes. In yet other embodiments, the pusher pulses may be applied only to every other pair of opposing short electrodes.

Figure 4A:
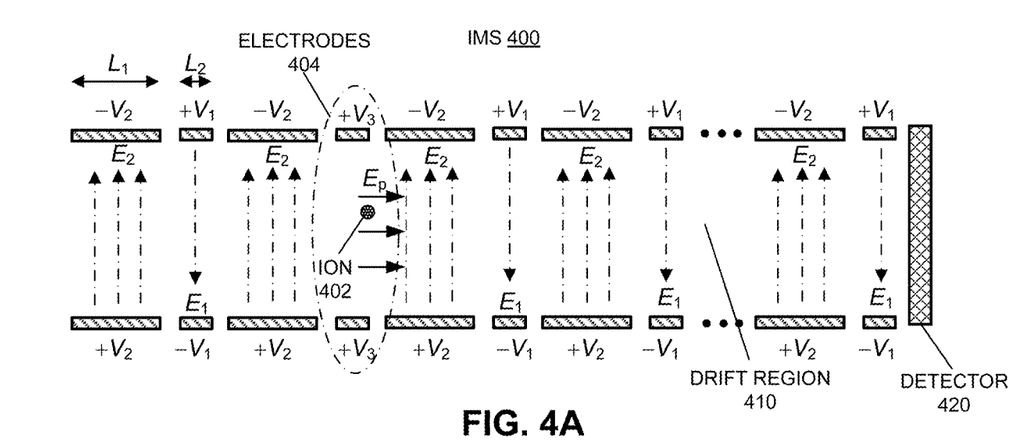
FIGS. 4A and 4B illustrate an IMS which uses timed pusher pulses for ion propulsion in accordance with an embodiment of the present disclosure.
Figure 4B:
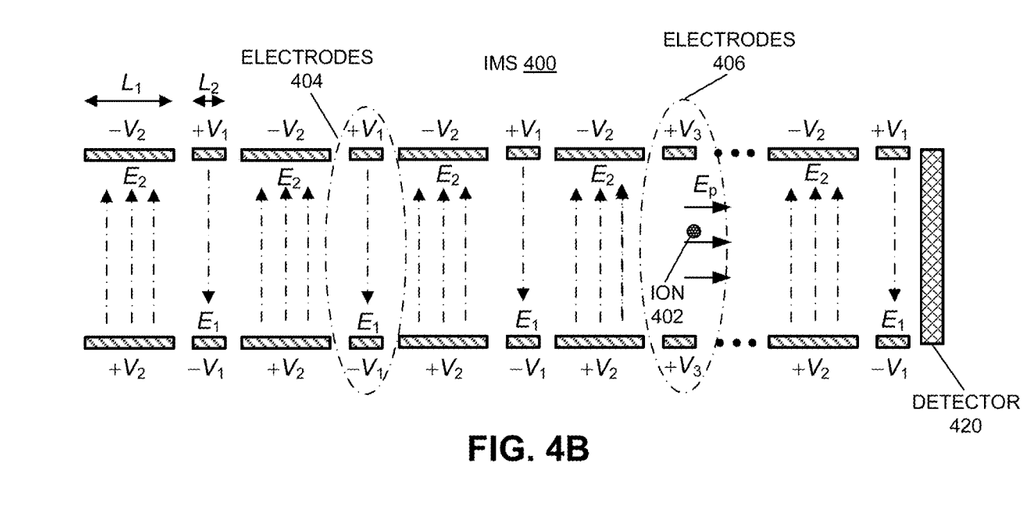

FIGS. 4A and 4B illustrate an IMS 400 which uses timed pusher pulses for ion propulsion in accordance with an embodiment of the present disclosure. Note that IMS device 400 does not require carrier gas for ion propulsion. As can be seen in FIG. 4A, IMS 400 comprises the same electrode configuration and substantially the same alternating DC field configuration as IMS 200. FIG. 4A shows that when positively charged particle 402 passes through the second pair of opposing short electrodes 404 and leaves the associated field region, the potentials on electrodes 404 instantly switch from $+V_1$ and $-V_1$ to a positive potential $+V_3$ on both the upper and lower electrodes. This creates an instantaneous field $E_p$ which will push the positive ion 402 to the right and cause it to continue on its directed path forward through drift region 410. In one embodiment, $+V_3=+V_1$.

FIG. 4B shows that when positively charged particle 402 passes through the fourth pair of opposing short electrodes 406 and leaves the associated field region, the potentials on electrodes 406 switch from $+V_1$ and $-V_1$ to the positive potential $+V_3$ on both upper and lower electrodes. This creates the instantaneous field $E_p$ which will push the positive ion 402 further to the right and cause it to continue on its directed path forward through drift region 410. Note that potentials on short electrodes 404 have switched back to normal $+V_1$ and $-V_1$. This process goes on until ion 402 reaches detector 420.

In some embodiments, the electrodes are connected in series, so the "even" and "odd" short electrodes are electrically connected, i.e., every other short electrode is electrically connected to each other and not connected to adjacent short electrodes. Hence, after an ion travels the distance from the short electrode with pusher potential to the next short electrode, the pusher potential is switched to the next short electrode. The pusher potential is alternated between two sets of "odd" and "even" electrodes with the gating delay equal to the drift time of the ion through a single set of long and short electrode region, until the ion reaches the detector. In one embodiment, the pusher pulse (height and duration) is adjusted so the velocity of the ion is maximized, while the electric field does not exceed zero field limit of ~1000 V/cm.

Note that timing the pusher pulses will gate ions with the correct mobility over the preset length of the drift region, allowing them to continue down to the next set of electrodes. The ions with lower or higher mobility than the correct one will be stopped by the gating pulse on one of the sets of short electrodes due to incorrect timing. Scanning the gating delay between the electrodes will produce an IMS spectrum of ion abundance vs. gating delay time, since the latter is a function of the ion's mobility. Hence, we may refer to the above-described ion propulsion and separation process as "timed" IMS.

Note that the ion propulsion and ion separation through timed IMS as described in conjunction with FIGS. 4A and 4B may be combined with the FAIMS process of ions moving through timing-varying high and low fields in a zigzag motion. In such devices, the device output can include a 3D plot of ion abundance vs. gating time (in the timed IMS) and CV (in the FAIMS process). In addition to the 3D plot, a fourth dimension can be added by scanning the high field to low field ratio ($E_h/E_l$) of the time-varying field by adjusting voltages on short and long electrodes simultaneously. This is analogous to RF scanning in conventional FAIMS.

Figure 5:
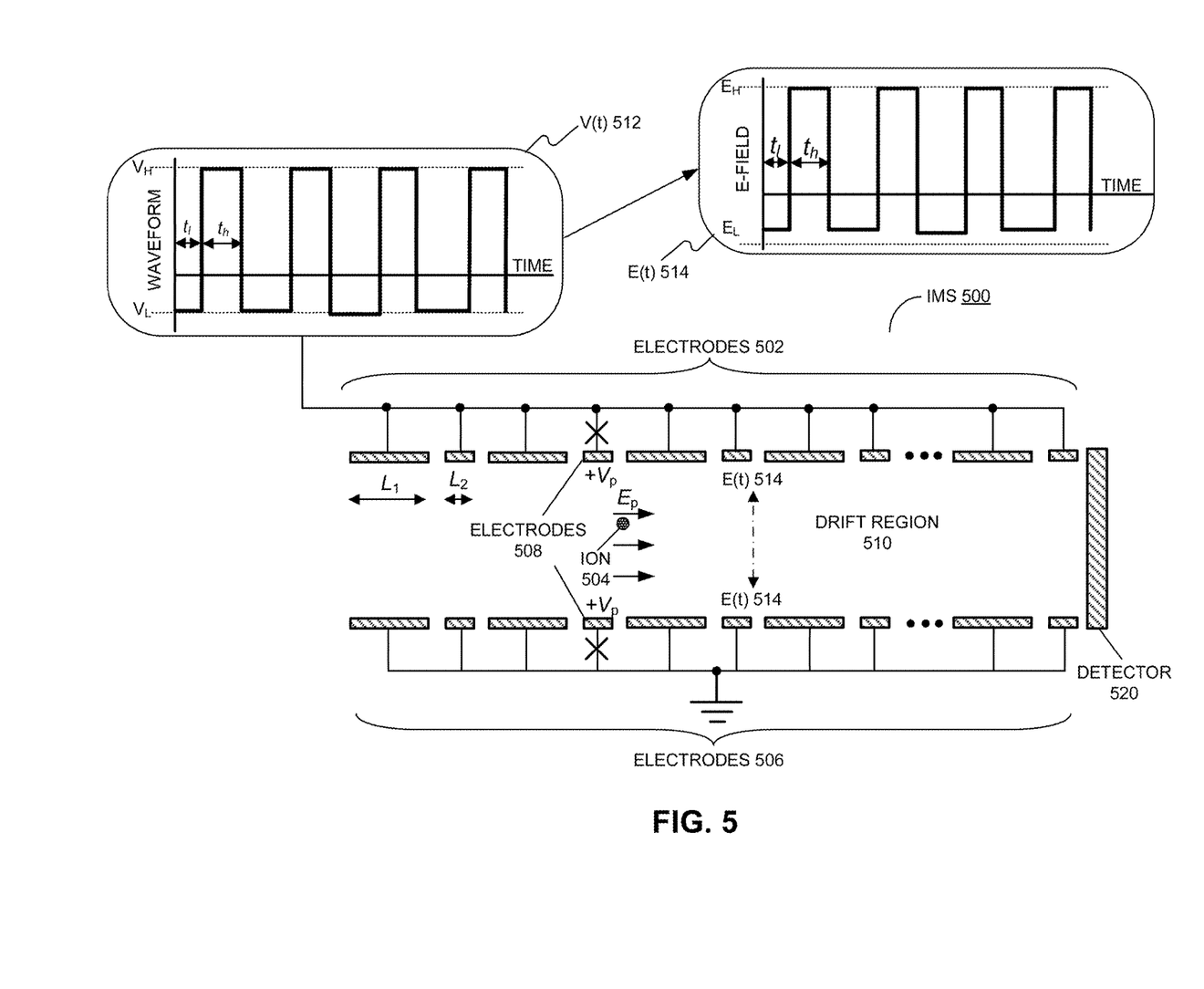
FIG. 5 illustrates an exemplary IMS which combines timed pusher pulses for ion propulsion and a FAIMS process in accordance with an embodiment of the present disclosure.

FIG. 5 illustrates an exemplary IMS 500 which combines timed pusher pulses for ion propulsion and a FAIMS process in accordance with an embodiment of the present disclosure. Note that IMS 500 does not require carrier gas for ion propulsion. As can be seen in FIG. 5, IMS 500 comprises substantially the same electrode configuration as IMS 200. However, electrically IMS 500 is configured more like a FAIMS device. More specifically, each of the lower set of electrodes 506 is grounded, while each of the upper set of electrodes 502 is connected to a time-varying potential V(t) 512 generated by a waveform generator (not shown), wherein V(t) 512 causes a timing-varying low and high-strength field E(t) 514 in drift region 510. Note that in other embodiments, the electrical connections of the two sets of electrodes are reversed.

FIG. 5 shows that when positively charged ion 504 passes through the second pair of opposing short electrodes 508 and leaves the associated field region, the potentials on both short electrodes 508 switch from a time-varying potential V(t) 512 and GND to the same positive potential $+V_p$. Note that this can be achieved by disconnecting the upper and lower electrodes 508 from the waveform generator and GND, while connecting both electrodes to potential $+V_p$. This creates an instantaneous pusher field $E_p$ which will propel positive ion 504 to the right and cause it to continue on its directed path forward through drift region 510 toward detector 520. Next, positive ion 504 is allowed to traverse either a single set of long and short electrode regions or multiple sets of long and short electrode regions before another pusher pulse is applied to the set of short electrodes which is traversed by positive ion 504. By combining timed IMS with the FAIMS process, the reduced ion residence time within the IMS device 500 is expected to lead to increased FAIMS resolution, because the number of FAIMS cycles is fixed and equal to the number of electrodes in the device.

One skilled in the art will appreciate that the resolution of each of the IMS devices described in conjunction with FIGS. 4-5 may be higher compared to classic FAIMS devices due to a very short ion residence time within the device because electrostatic techniques rather than aerodynamic techniques are used for ion propulsion. Depending on the pusher potential values used for the ion propulsion, the ion can be cleared from the device in an order of microseconds or faster. For a simple design, it is possible to use a defined number of short/long electrode sets, which in turn will result in a preset number of FAIMS cycles that an ion undergoes. This will limit the resolution of the device because the number of FAIMS cycles an ion can undergo is equal to the number of electrodes. In a more sophisticated design of the device, the ion path can be increased to gain higher FAIMS resolution via implementing ion multi-passing through the device by suitable reflection ion optics.

Figure 6:
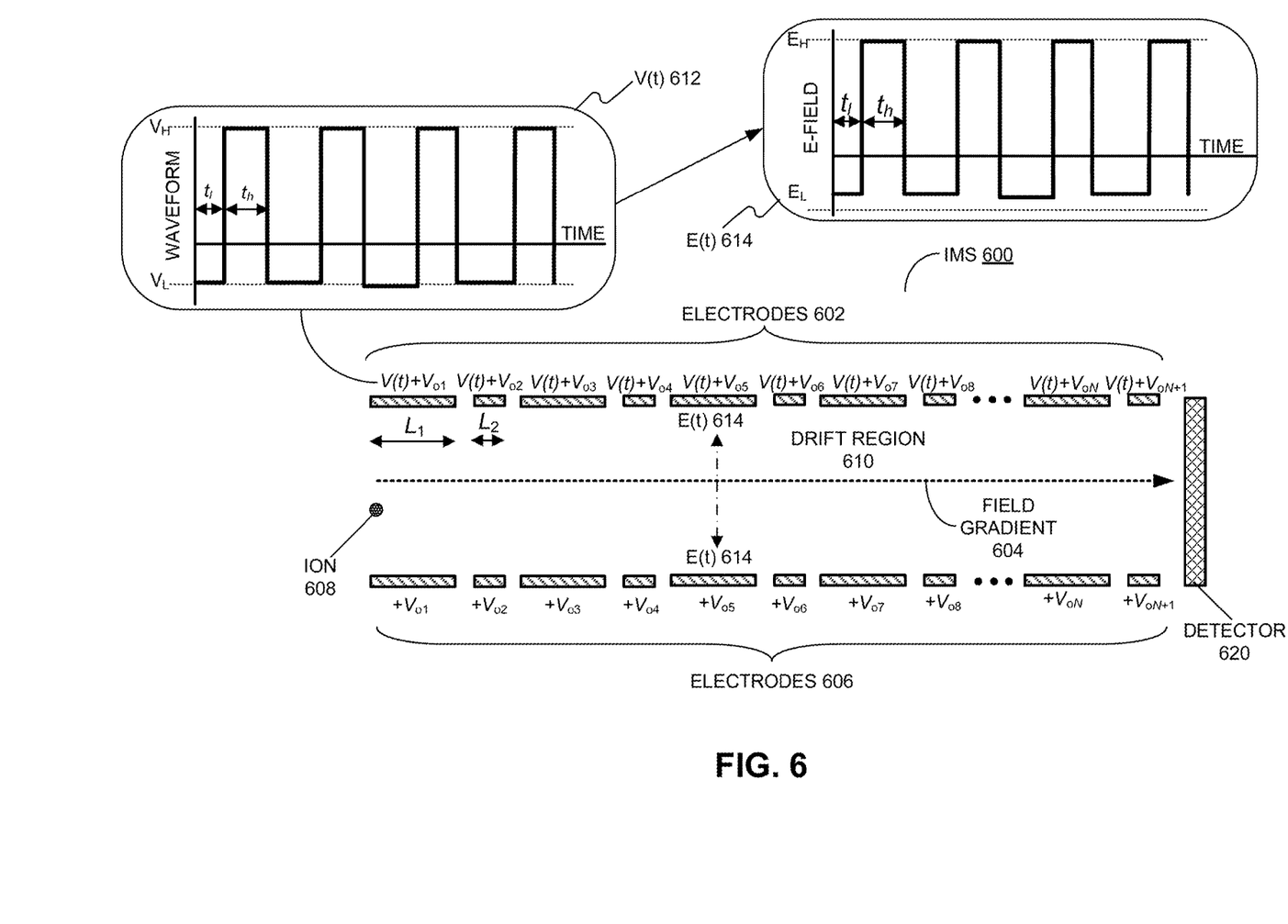
FIG. 6 illustrates an exemplary IMS which combines field gradient with a FAIMS process in accordance with an embodiment of the present disclosure.

Note that the ion propulsion through field gradient as described in conjunction with FIG. 3 may be combined with the FAIMS process of ions moving through timing-varying high and low fields in a zigzag motion. FIG. 6 illustrates an exemplary IMS 600 which combines a field gradient with a FAIMS process in accordance with an embodiment of the present disclosure. Again, IMS 600 does not require carrier gas to propel ions.

As can be seen in FIG. 6, IMS 600 comprises substantially the same electrode configuration as IMS 200. Electrically, the potential on each of the upper set of electrodes 602 includes the time-varying potential V(t) 612 generated by a waveform generator, wherein V(t) 612 causes a timing-varying low and high-strength field E(t) 614 in drift region 610. The potential on each of the upper set of electrodes 602 also includes a DC offsets, (i.e., $+V_{o1}$, $+V_{o2}$, $+V_{o3}$, etc.) in decreasing value from left to right. The potential on each of the lower set of electrodes 606 includes only the DC offset, (i.e., $+V_{o1}$, $+V_{o2}$, $+V_{o3}$, etc.) in decreasing value from left to right to match the DC offset on the corresponding upper electrodes 602. Hence, the DC offsets on both the upper and lower sets of electrodes 602 and 606 create field gradient 604 which points from left to right within drift region 610, which will facilitate sweeping a positive ion 608 from left to right through drift region 610 toward detector 620. Meanwhile, the FAIMS process causes positive ion 608 to move in the zigzag motion through timing-varying high and low field regions.

Figure 7:
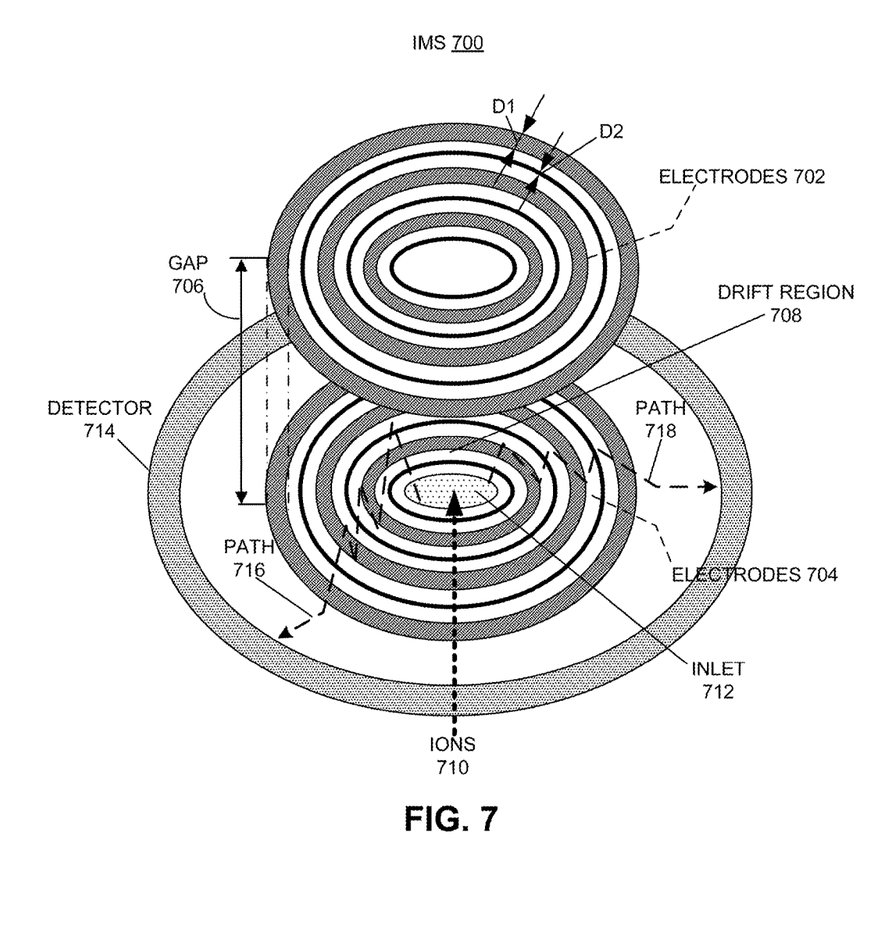
FIG. 7 presents a 3-dimensional (3D) view of a SAAF IMS configured with concentric-ring electrodes that allows ions to travel radially in accordance with an embodiment of the present disclosure.

Note that while the SAAF IMS embodiments of FIGS. 2-6 present discrete electrodes configurations that facilitate ions travel linearly from one end of the drift region to the other end of the drift region, other SAAF IMS variations can have discrete electrodes configured so that ion travels in radially direction. FIG. 7 presents a 3D view of a SAAF IMS 700 configured with concentric-ring electrodes that allows ions to travel radially in accordance with an embodiment of the present disclosure.

As can be seen in FIG. 7. SAAF IMS 700 comprises an upper set of discrete electrodes 702 and a lower set of discrete electrodes 704 separated by a gap 706, and a drift region 708 formed between the two sets of electrodes. Each set of electrodes 702 is formed by a set of concentric ring electrodes that alternate between a wider ring width $D_1$ and a narrow ring width $D_2$. Ions can be introduced into drift region 708 from either above or below SAAF IMS 700 near the center of drift region 708. In the embodiment shown, ions 710 enter from below the device through an inlet 712 near the center of the lower set of discrete electrodes 704.

Although not shown, the two sets of electrodes 702 and 704 may be biased with one of the various electrical configurations described in conjunction with FIGS. 2-6. Hence, ions 710 experience a drift within drift region 708 from the inner rings of electrodes 702 and 704 radially toward the outer rings of the electrodes 702 and 704, and eventual reach ring detector 714 positioned outside SAAF IMS 700. Note that different ions 710 may travel in different radial paths, e.g., path 716 and 718. Ions 710 will also displace up and down alternately toward the upper electrodes 702 and the lower electrodes 704 as they traverse drift region 708, thereby allowing ions to be separated.

Referring back to FIG. 2A, while we have described different techniques of propelling ions through drift region 210 without using carrier gas, one embodiment can combine SAAF IMS 200, which is configured with spatially alternating field polarity and field strength with a carrier gas ion propulsion system.

In one embodiment, the discrete electrodes configuration shown in IMS 200 can be electrically configured into a FAIMS device and include a conventional carrier gas ion propulsion system.

In one embodiment, the discrete electrodes configuration shown in IMS 600 can be electrically configured with only the offset potentials to create field gradient 604 without the additional waveform V(t). This way, we obtain a traditional drift time IMS (by measuring ion fly time) without FAIMS or SAAF. Note that the various IMS devices described above are largely made possible as a result of using discrete electrodes.

Note that for each of the embodiments of IMS 300 in FIG. 3, IMS 600 in FIG. 6, and the traditional drift time IMS obtained from IMS 600 described above, ion propulsion within the drift tube is caused by a field gradient, which allows for the ion abundance vs. drift time IMS measurement. In each of these embodiments, an additional degree of ion separation can be achieved by placing an ion gating module, such as a Bradbury-Nielsen shutter, at the ion inlet of the respective IMS device. In doing so, the device output can include a 3D plot of ion abundance vs. the drift time (through the drift time IMS) and ion deflections (through the ion gating). Note that a Bradbury-Nielsen shutter for such applications can be micromachined and implemented on a chip using microelectromechanical systems (MEMS) techniques.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. An ion mobility spectrometry (IMS) device for performing chemical analysis, comprising:
 a first set of electrodes arranged linearly in a first direction and separated by a first set of gaps;
 a second set of electrodes positioned directly opposing the first set of electrodes to match the first set of electrodes on a one-to-one basis, wherein the second set of electrodes are separated by a second set of gaps;
 a drift region between the first set of electrodes and the second set of electrodes, wherein charged particles enter at a first end of the drift region and traverse the drift region along the first direction; and
 a detector positioned at a second end of the drift region configured to receive charged particles exiting the drift region;
 wherein a first electrode in the first set of electrodes and a matching first electrode in the second set of electrodes are configured to generate a static first electric field perpendicular to the first direction;
 wherein a second electrode in the first set of electrodes and a matching second electrode in the second set of electrodes are configured to create a static second electric field perpendicular to the first direction and having an opposite polarity to the first electric field; and
 wherein the first set of electrodes and the second set of electrodes are configured to create a static field pattern which spatially alternates between the first electric field and second electric field along the first direction;
 wherein the first set of electrodes comprises electrodes which alternate between a first length and a second length that is less than the first length, wherein the first electrode in the first set of electrodes is of the first length; and wherein the second electrode in the first set of electrodes is of the second length; and
 wherein the second set of electrodes comprises matching electrodes which alternate between the first length and the second length, wherein the matching first electrode in the second set of electrodes is of the first length; and wherein the matching second electrode in the second set of electrodes is of the second length;
 wherein at least the first electrode and a third electrode in the first set of electrodes is configured to have a static voltage $V_A$, wherein at least the matching first electrode and a third electrode in the second set of electrodes is configured to have a static voltage $V_B$, wherein at least the second electrode and a fourth electrode in the first set of electrodes is configured to have a static voltage $V_C$, and wherein at least the matching second electrode and fourth electrode in the second set of electrodes is configured to have a static voltage $V_D$;
 wherein $V_A$, $V_B$, $V_C$ and $V_D$ are set to four different static voltage levels to facilitate operation of the IMS device;
 wherein the first and second sets of electrodes comprise planar electrodes fabricated through a micro-fabrication process on the same wafer, wherein a spacing between the first and second sets of electrodes ranges from a few microns to a few hundred microns, whereby voltages $V_A$–$V_B$ and $V_C$–$V_D$ that range from 1V to 20 V suffice to generate the first and second static electric fields with sufficient strength to facilitate ion separation without a waveform generator.

2. The IMS device of claim 1, wherein the spatially alternating first electric field and second electric field are configured to cause charged particles of different mobility dependences on the first and second electric fields to separate by deflecting toward one of the first and second sets of electrodes while traversing the drift region.

3. The IMS device of claim 1, wherein the spatially alternating first electric field and second electric field are configured so that charged particles of different mobility dependences are separated while traversing the full length of the drift region.

4. The IMS device of claim 1, wherein a compensating voltage (CV) is configured to be applied to all of the electrodes in the first set of electrodes or the second set of electrodes to correct a path of a charged particle to allow the charged particle to exit the drift region in such a way as to hit the detector.

5. The IMS device of claim 1, wherein a subset of electrodes in the first set of electrodes and the matching electrodes in the second set of electrodes are configured to be coupled to a set of offset voltages to create an electric field gradient through the drift region for propelling the charged particles.

6. The IMS device of claim 1, wherein the first set of gaps is a first constant gap and the second set of gaps is a second constant gap, and wherein the first constant gap is substantially equal to the second constant gap.

7. The IMS device of claim 1, wherein the IMS device is configured to output the following signals associated with a given type of ion:
 a drift time;
 a compensation voltage associated with a differential mobility-based parameter; and
 an ion abundance parameter.

8. The IMS device of claim 1, further comprising ion reflectrons positioned at both ends of the drift region, wherein the ion reflectrons are configured to reflect the arriving charged particles back through the drift region to enhance the resolution of differential mobility separation.

9. The IMS device of claim 8, wherein the ion reflectrons are configured to control a number of times that the charged particles are reflected into the drift region to achieve the required level of separation before being allowed to reach the detector.

10. The IMS device of claim 1, wherein the IMS device further comprises a driving mechanism positioned at the first end of the drift region and configured to drive the charged particles into the drift region.

11. The IMS device of claim 1,
wherein the first set of electrodes is disposed on a first electrode plane;
wherein the second set of electrodes is disposed on a second electrode plane; and
wherein the distance between the first electrode plane and the second electrode plane determines a gap between each pair of opposing electrodes.

12. The IMS device of claim 1, wherein the first set of electrodes and the second set of electrodes are separated by a constant gap.

13. The IMS device of claim 1, wherein the IMS device further comprises an ion gating module positioned at the first end of the drift region and configured to selectively deflect the charged particles entering the drift region.

14. The IMS device of claim 13, wherein the ion gating module is a Bradbury-Nielsen shutter.

15. The IMS device of claim 1,
wherein $V_A$ is a positive static voltage $+V_2$;
wherein $V_B$ is a negative static voltage $-V_2$,
wherein $V_c$ is a positive static voltage $+V_1$; and
wherein $V_D$ is a negative static voltage $-V_1$.

16. The IMS device of claim 1,
wherein $V_A$ is a positive static voltage $+V_2+V_{o1}$, wherein $V_{o1}$ is an offset voltage;
wherein $V_B$ is a negative static voltage $-V_2+V_{o1}$,
wherein $V_c$ is a positive static voltage $+V_1+V_{o2}$, wherein $V_{o2}$ is an offset voltage; and
wherein $V_D$ is a negative static voltage $-V_1+V_{o2}$.

17. A method for operating an ion mobility spectrometry (IMS) device for performing chemical analysis, wherein the IMS device includes, a first set of electrodes arranged linearly in a first direction and separated by a first set of gaps, a second set of electrodes positioned directly opposing the first set of electrodes to match the first set of electrodes on a one-to-one basis, wherein the second set of electrodes are separated by a second set of gaps, a drift region between the first set of electrodes and the second set of electrodes, wherein charged particles enter at a first end of the drift region and traverse the drift region along the first direction, and a detector positioned at a second end of the drift region configured to receive charged particles exiting the drift region, the method comprising:
operating the IMS device;
wherein during operation of the IMS device, a first electrode in the first set of electrodes and a matching first electrode in the second set of electrodes generate a static first electric field perpendicular to the first direction;
wherein during operation of the IMS device, a second electrode in the first set of electrodes and a matching second electrode in the second set of electrodes create a static second electric field perpendicular to the first direction and having an opposite polarity to the first electric field; and
wherein during operation of the IMS device, the first set of electrodes and the second set of electrodes create a static field pattern which spatially alternates between the first electric field and second electric field along the first direction;
wherein during operation of the IMS device, wherein at least the first electrode and a third electrode in the first set of electrodes is configured to have a static voltage $V_A$, wherein at least the matching first electrode and a third electrode in the second set of electrodes is configured to have a static voltage $V_B$, wherein at least the second electrode and a fourth electrode in the first set of electrodes is configured to have a static voltage $V_c$, and wherein at least the matching second electrode and fourth electrode in the second set of electrodes is configured to have a static voltage $V_D$;
wherein $V_A$, $V_B$, $V_c$ and $V_D$ are set to four different static voltage levels to facilitate operation of the IMS device;
wherein the first and second sets of electrodes comprise planar electrodes fabricated through a micro-fabrication process on the same wafer, wherein a spacing between the first and second sets of electrodes ranges from a few microns to a few hundred microns, whereby voltages $V_A$-$V_B$ and $V_c$-$V_D$ that range from 1V to 20 V suffice to generate the first and second static electric fields with sufficient strength to facilitate ion separation without a waveform generator.

18. The method of claim 17,
wherein $V_A$ is a positive static voltage $+V_2$;
wherein $V_B$ is a negative static voltage $-V_2$,
wherein $V_c$ is a positive static voltage $+V_1$; and
wherein $V_D$ is a negative static voltage $-V_1$.

* * * * *